United States Patent
Phaneuf et al.

(10) Patent No.: US 6,743,253 B2
(45) Date of Patent: Jun. 1, 2004

(54) POLYURETHANE-SEALED BIOCOMPATIBLE DEVICE AND METHOD FOR ITS PREPARATION

(75) Inventors: Matthew D. Phaneuf, Ashland, MA (US); Donald J. Dempsey, Newbury, MA (US); William C. Quist, Brookline, MA (US); Frank W. Logerfo, Belmont, MA (US)

(73) Assignees: BioMod Surfaces, Salisbury, MA (US); Beth Israel Deaconess Medical Center, Boston, MA (US)

( * ) Notice: Subject to any disclaimer, the term of this patent is extended or adjusted under 35 U.S.C. 154(b) by 0 days.

(21) Appl. No.: 09/796,569

(22) Filed: Feb. 28, 2001

(65) Prior Publication Data

US 2001/0053933 A1 Dec. 20, 2001

Related U.S. Application Data

(60) Provisional application No. 60/186,154, filed on Feb. 29, 2000.

(51) Int. Cl.[7] .................................................. A61F 2/06
(52) U.S. Cl. ...................... 623/1.46; 623/1.42; 623/1.52
(58) Field of Search ............................... 623/1.42, 1.43, 623/1.44, 1.46, 1.48, 1.5, 1.51, 1.52

(56) References Cited

U.S. PATENT DOCUMENTS

| | | | |
|---|---|---|---|
| 3,953,566 A | | 4/1976 | Gore .......................... 264/288 |
| 4,164,045 A | * | 8/1979 | Bokros et al. .............. 442/164 |
| 4,187,390 A | | 2/1980 | Gore .......................... 174/102 |
| 4,743,252 A | * | 5/1988 | Martin et al. .............. 623/1.44 |
| 5,429,618 A | * | 7/1995 | Keogh ......................... 604/266 |
| 5,628,788 A | * | 5/1997 | Pinchuk ....................... 623/1.2 |
| 5,830,539 A | * | 11/1998 | Yan et al. ................... 427/2.13 |
| 5,853,744 A | * | 12/1998 | Mooradian et al. ......... 424/422 |
| 5,866,113 A | * | 2/1999 | Hendriks et al. ........... 424/486 |
| 5,925,552 A | * | 7/1999 | Keogh et al. .............. 424/178.1 |
| 6,033,719 A | * | 3/2000 | Keogh ........................ 427/2.12 |
| 2002/0055710 A1 | * | 5/2002 | Tuch ...................... 604/103.02 |
| 2002/0065546 A1 | * | 5/2002 | Machan et al. ............ 623/1.13 |

OTHER PUBLICATIONS

Berceli, S. A. et al., "Evaluation of a Novel Hirudin–coated Polyester Graft to Physiologic Flow Conditions: Hirudin Bioavailability and Thrombin Uptake," *J. Vasc. Surg.* 27:1117–1127 (1998).

Collier, T. et al., "Biocompatibility of Poly(Etherurethane Urea) Containing Dehydroepiandrosterone," *J. Biomed. Mater. Res.* 41:192–201 (1998).

Comerota, A. J. et al., "Graft Thrombosis and Thromboembolic Complications," *Vascular Surgery* 4th *Edition*, 571–587, Rutherford R. W. ed., W. B. Saunders Co., Philadelphia, PA (1995).

Dempsey, D. J. et al., "Synthesis of a Novel Small Diameter Polyurethane Vascular Graft with Reactive Binding Sites," *ASAIO J.* 44:M506–M510 (1998).

Fyfe, B. et al., "Pathologic Analysis of 34 Explained Symbion Ventricular Assist Devices and 10 Explanted Jarvik–7 Total Artificial Hearts," *Cardiovasc. Path* 2:187–197 (1993).

Hanson, S. R. "Device Thrombosis and Thromboembolism," in *Cardiovascular Pathology,* 157S–165S, Harker, L. A. et al. ed., Elsevier Science Publishing Co, Inc., New York, New York (1993).

(List continued on next page.)

*Primary Examiner*—Corrine McDermott
*Assistant Examiner*—William H Matthews
(74) *Attorney, Agent, or Firm*—Clark & Elbing LLP; Paul T. Clark

(57) ABSTRACT

Provided is a biocompatible device which has been coated or sealed with a polyether or polyether/carbonate based urethane polymer that contains functional groups (e.g. carboxylic acid groups) which are capable of serving as anchor sites for protein binding.

19 Claims, 4 Drawing Sheets-

Lumenal Surface

Capsular Surface

OTHER PUBLICATIONS

Kadoba, K. et al., "Experimental Comparison of Albumin--sealed and Gelatin-sealed Knitted Dacron Conduits, Porosity Control, Handling, Sealant Resorption, and Healing," *J. Thorac. Cardiovasc. Surg.* 103:1059–1067 (1992).

Kottke-Marchant, K. et al., "Effect of Albumin Coating on the In Vitro Blood Compatibility of Dacron Arterial Prostheses," *Biomaterials* 10:147–155 (1989).

Kubaska, S. M., III et al., "Characterization of Covalently Bound Vascular Endothelial Growth Factor: Creation of a Novel Dacron Prosthetic Graft Surface," *Surgical Forum* 49:322–324 (1998).

Lin, H. B. et al., "Synthetic, Surface, and Cell–adhesion Properties of Polyurethane Containing Covalently Grafted RGD–peptides," *J. Biomed. Mater. Res.* 28:329–343 (1994).

LoGerfo, F. W. et al., "Downstream Anastomotic Hyperplasia. A Mechanism of Failure in Dacron Arterial Grafts," *Ann. Surg.* 197:479–483 (1983).

Park, K. D. et al., "Heparin Immobilization onto Segmented Polyurethane–urea Surfaces—Effect of Hydrophilic Spacers," *J. Biomed. Mater. Res.* 22:977–992 (1988).

Phaneuf, M. D. et al., "Bioengineering of a Novel Small Diameter Polyurethane Vascular Graft with Covalently Bound Recombinant Hirudin," *ASAIO J.* 44:M653–M658 (1998).

Phaneuf, M. D. et al., "Chemical and Physical Characterization of a Novel Poly(Carbonate Urea) Urethane Surface with Protein Crosslinker Sites," *J. Biomed. Appl.* 12:100–120 (1997).

Phaneuf, M. D. et al., "Covalent Linkage of Recombinant Hirudin to Poly(Ethylene Terephthalate) (Dacron): Creation of a Novel Antithrombin Surface," *Biomaterials* 18:755–765 (1997).

Phaneuf, M. D. et al., "Modification of Polyurethane Terephthalate (Dacron) via Denier Reduction: Effects on Material Tensile Strength, Weight, and Protein Binding Capabilities," *J. Applied Biomater.* 6:289–299 (1995).

Phaneuf, M. D. et al., "Covalent Linkage of Streptokinase to Recombinant Hirudin: A Novel Thrombolytic Agent with Antithrombiotic Properties," *Thromb. Haemost.* 71:481–487 (1994).

Rumisek, J. et al., "The Influence of Early Surface Thromboreactivity on Long–term Arterial Graft Patency," *Surgery* 105:654–661 (1989).

Saywer, P. N. et al., "In Vitro and In Vivo Evaluations of Dacron Velour and Knit Prostheses," *J. Biomed. Mater. Res.* 13:937–956 (1979).

Schubert, M. A. et al., "Student Research Award in the Doctoral Degree Candidate Category, Fifth World Biomaterials Congress ($22^{nd}$ Annual Meeting of the Society for Biomaterials), Toronto, Canada, May 29–Jun. 2, 1996. Vitamin E as an Antioxidant for Poly(etherurethane urea): In Vivo Studies," *J. Biomed. Mater. Res.* 32:493–504 (1996).

Ward, R. S. et al., "The Effects of Phase Separation and End Group Chemistry on the In Vivo Biostability of Polyurethanes" *Trans ASAIO Meeting*, Washington, D.C., Lippincott–Raven, Philadelphia, PA (Abstract) (1996).

Zhang, Z. et al., "Removing Fresh Tissue from Explained Polyurethane Prostheses: Which Approach Facilitates Physico–chemical Analysis," *Biomaterials* 16:369–380 (1995).

Zhao, Q. et al., "Glass Wool–$H_2O_2$/$CoCI_2$ Test System for In Vitro Evaluation of Biodegradative Stress Cracking in Polyurethane Elastomers," *J. Biomed. Mater. Res.* 29:467–475 (1995).

\* cited by examiner

Lumenal Surface

Capsular Surface

POLYURETHANE-SEALED BIOCOMPATIBLE DEVICE AND METHOD FOR ITS PREPARATION

This application claims priority from U.S. Ser. No. 60/186,154, which was filed on Feb. 29, 2000.

STATEMENT OF FEDERALLY SPONSORED RESEARCH

This invention was made with government support under a grant entitled DEVELOPMENT OF A BIOLOGICALLY-ACTIVE VASCULAR GRAFT/1R41HL63511-01A1 awarded by the National Heart, Lung, and Blood Institute through a Small Business Technology Transfer Research Program. The government has certain rights to the invention.

BACKGROUND OF THE INVENTION

This invention relates to biocompatible devices and the methods and materials used to make them. More particularly, the invention relates to synthetic vascular grafts.

Synthetic vascular prostheses have been widely used in clinical medicine as replacements and bypasses for large, medium, and small vessels in human patients. These prostheses are often used when the patient lacks adequate autogenous replacement tissue due to prior chemotherapy, previous harvesting, phlebitis, or other vascular pathologies.

Vascular grafts of medium (6–8 mm) and small (<5 mm) internal diameter are primarily utilized in peripheral regions of the body and appendages. Despite recent advancements in the materials used to make vascular grafts, medium and small diameter grafts continue to have unacceptably high failure rates when used in the clinical setting. The major complications associated with these grafts include: (1) structural and mechanical degradation (Hanson, S. R. In *Cardiovasc. Pathology* 157S–165S, Harker, L. A., et al. ed., Elsevier Science Publishing Co. Inc., New York, N.Y. (1993)), (2) acute thrombosis and thromboembolic phenomenon (Fyfe, B., et al. *Cardiovasc. Path.* 2:187 (1993)), and (3) incomplete, unregulated, or inappropriate cellular healing (Kaboda, K., et al. *J. Thorac. Cardiovasc. Surg.* 103:1059 (1992)). Failure of prosthetic arterial grafts can be grouped into three categories: acute, delayed, and late. An acute failure (occurring within hours or days after implantation) is generally the result of reduced blood flow through the luminal surface of the graft, resulting in increased activation of the coagulation cascade with subsequent thrombosis or thromboembolic phenomenon occurring (Hanson, S. R. In *Cardiovasc. Pathology* 157S–165S, Harker, L. A., et al. ed., Elsevier Science Publishing Co. Inc., New York, N.Y. (1993)). A delayed failure (occurring within weeks or months after implantation) is generally caused by an incomplete endothelial cell lining of the graft surface, resulting in uncontrolled vascular smooth muscle cell proliferation (LoGerfo, F. W., et al. *Ann. Surg.* 197:479 1983). Late graft failure (occurring within years after implantation) is infrequent and most often due to progression of atherosclerosis in the inflow or outflow vessels.

Expanded polytetrafluoroethylene (ePTFE) is currently one of the most widely used materials for vascular grafts. See, e.g., U.S. Pat. Nos. 4,187,390 and 3,953,566. However, the chemical structure of ePTFE is extremely rigid, thereby creating a mechanical mismatch at the interface between the native artery and the graft. Additionally, surface modification of ePTFE grafts is generally not possible due to the inertness of the polymer.

Polyethylene terephthalate (polyester or Dacron™) vascular grafts, which have better mechanical (i.e. stretching) and handling (i.e. suturing) properties than ePTFE grafts, have had limited use. These grafts have a porous graft matrix that is typically sealed with proteins purified from another species, e.g. porcine, bovine, etc., that are randomly cross-linked by fixative agents such as glutaraldehyde and formaldehyde. These protein-coated surfaces help to "mask" the graft from immune response. However, they have numerous adverse effects in vivo, including platelet adhesion and activation with the release of growth factors and pro-thrombotic molecules, and are rapidly desorbed, potentially re-exposing the biomaterial surface.

Due to the problems associated with conventional synthetic vascular grafts, they are generally unsuitable for smaller diameter vascular reconstructions. Thus, there remains a need to develop biocompatible synthetic vascular prostheses that have physical and chemical properties that more closely approximate those of autogenous blood vessels. In particular, there is a need to develop vascular grafts suitable for use in medium and small diameter arterial reconstructions.

SUMMARY OF THE INVENTION

The present invention features a polyether or polyether/carbonate based urethane polymer that contains functional groups (e.g. carboxylic acid groups) which are capable of serving as anchor sites for protein binding. The polymer is prepared using a process that includes the following two steps: (1) forming a diisocyanate terminated prepolymer, based on a polyether or polyether/carbonate glycol that has a molecular weight between 200–3,000 Da (preferably about 1000 Da), and a diisocyanate having the general structure OCN—R'—NCO, wherein R' is a hydrocarbon that may include aromatic or non-aromatic structures; and (2) chain extension using a dihydroxy carboxylic acid, for example, 2,2-bis(hydroxymethyl)-propionic acid (DHMPA).

The invention also features a biocompatible device that has been sealed with the polyether or polyether/carbonate based urethane polymer. The biocompatible device can be, for example, a polyethylene terephthalate (polyester or Dacron™) vascular graft or other polymeric base material. The surface properties of the graft can be modified with biologically active proteins in order to emulate certain natural properties of native vessels, thereby improving graft patency and healing. For instance, antithrombin (recombinant hirudin) or other anti-clotting agents, thrombolytic agents (e.g. streptokinase, urokinase, tPA, pro-urokinase, etc.), and mitogenic agents (e.g. vascular endothelial growth factor) or other growth promoting substances, or inhibitors (e.g. γ-interferon) can be linked to the surface of the graft.

In another aspect, the invention provides a technique for sealing a vascular graft, such as a polyethylene terephthalate vascular graft, with polyurethane using an inward/luminal perfusion system. The perfusion system includes a flow chamber which has inflow and outflow fixtures and a hollow inner mandrel. The system also includes a Y-fitting that is connected to the flow chamber and a peristaltic pump via hollow plastic tubing. The Y-fitting is also connected to a container holding a polyurethane sealant solution.

DETAILED DESCRIPTION

Figure 1:
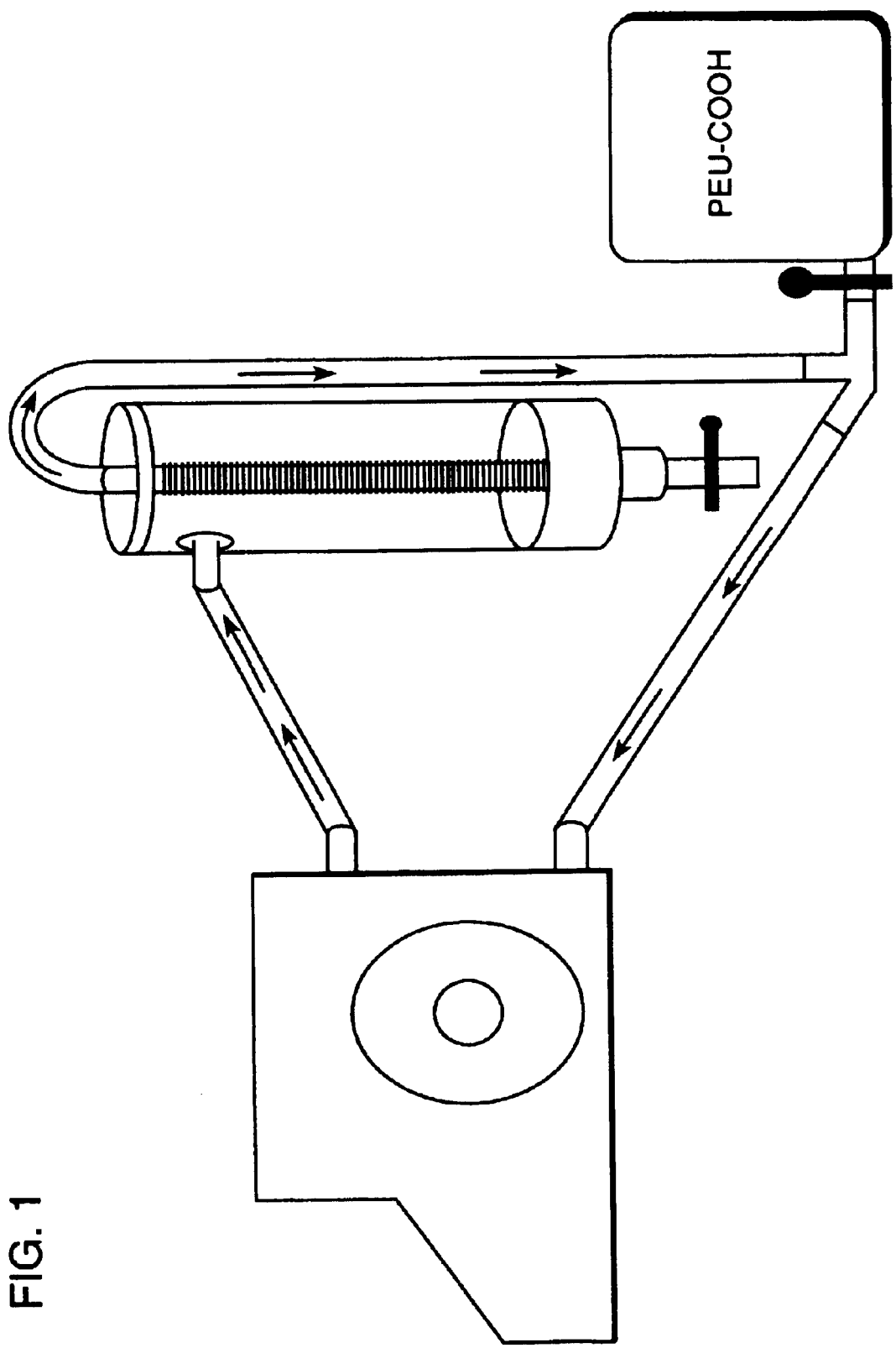
FIG. 1 is a diagram of a perfusion system adapted to incorporating PEU-COOH throughout the wall of a vascular graft.

The invention features a biocompatible device which has been coated or sealed with a polyether or polyether/carbonate based urethane polymer. The polyurethane compound of the invention contains functional groups (e.g. carboxylic acid groups) which are capable of serving as anchor sites for protein binding. This polyurethane possesses more compliant mechanical properties (i.e. elasticity) than previously utilized polycarbonate-based urethanes.

The biocompatible device of the invention is intended to contact cells, biological fluids, or preparations derived from cells. In one embodiment, the biocompatible device is a vascular graft prosthesis. Vascular grafts of the invention are preferably biodurable, non-thrombogenic, chemically durable, resistant to infection or formation of microbial plaques, easy to implant, and possess appropriate elastic properties.

Biocompatible materials suitable for use in the vascular grafts of the invention can be any materials that do not activate coagulation or inhibit cellular healing. The material should be sufficiently malleable so that it can form the appropriate geometry, but also have sufficient tensile strength to endure rigorous circulation throughout the vascular tree. The biocompatible material should be able to be sterilized, for example, by gamma radiation. The biocompatible materials useful in the present invention include, but are not limited to, polyethylene terephthalate (Dacron™ or polyester), nylon, polyurethane, Kevlar™, polyethylene, polypropylene, silicons, and combinations thereof.

Standard Dacron™ vascular grafts are predominantly employed for large-diameter arterial reconstructions (i.e., internal diameter (ID) greater than 9 mm), such as thoracic or abdominal aorta reconstructions. A majority of these grafts are sealed with cross-linked collagen (e.g. HEMASHIELD™) in order to prevent pre-clotting the graft interstices with the patient's blood. This sealing procedure often creates a highly thrombogenic surface. Blood flow through these larger arteries is significantly higher than other areas within the peripheral vascular tree (e.g., the iliac and femoral arteries), therefore grafts implanted at these sites generally have greater than 90% patency rates. Implantation of conventional Dacron™ grafts in peripheral or medium-diameter arteries (i.e., internal diameter between 6–8 mm) results in a significant reduction in patency (20–40%) (see, e.g., Comerota, A. J., et al. "Graft thrombosis and thromboembolic complications" in *Vascular Surgery*, $4^{th}$ Ed., Rutherford, R. W. ed., W. B. Saunders Co., Philadelphia (1995)).

Prosthetic grafts made from ePTFE are used for both large and medium-diameter arterial reconstructions. No difference in patency rates between Dacron™ and ePTFE grafts in large-diameter implants has been demonstrated. In medium-diameter reconstructions, however, ePTFE has slightly higher patency than Dacron™. In general, neither of these types of graft material are used clinically for small-diameter arterial grafting (i.e., internal diameter of less than 5 mm) due to poor patency rates (less than 20% patency within the first year).

In a preferred embodiment, the biocompatible device of the present invention is a polyethylene terephthalate (Dacron™) vascular graft. The graft is sealed with polyurethane preferably using an inventive sealing technique, with permeation controlled by the methodology. The final composite graft of the invention has permeation values comparable to that of a protein-sealed vascular graft. The preferred polyurethane sealant has functional groups (e.g. carboxylic acid groups) within the polymer backbone to which proteins can be covalently attached. The functional groups on the graft surface are accessible to protein binding, with less non-specific protein adhesion than a standard Dacron™ prosthesis. The polyurethane-sealed graft of the invention has good handling characteristics, self-sealing properties, and healing characteristics comparable to a standard protein-sealed Dacron™ prosthesis, but without the adverse effects associated with conventional protein-sealed grafts. These improved characteristics enable the graft to be used not only in large-diameter vascular reconstructions, but also in medium and small-diameter reconstructions.

Studies on the mechanisms of prosthetic arterial graft failure have revealed that all biomaterials are excluded from direct blood interaction within minutes of establishing blood flow by an amorphous pseudointima composed of platelets, fibrin, fibrinogen, and serum proteins. LoGerfo, F. W., et al., *Ann. Surg.* 197:479 (1983). Thus, it is desirable to have a biomaterial surface which will alter pseudointima composition and formation. Furthermore, biomaterials interpositioned in the vasculature must address two key components of vascular graft biology: (1) activation of the coagulation cascade and (2) incomplete cellular healing. Since the polyurethane sealant of the present invention possesses functional groups which permit covalent linkage of protein, the surfaces of implants sealed with this polyurethane can be designed so that selected biologically-active proteins can be immobilized in order to localize the beneficial effects directly on the material surface. Thus, both antithrombin and mitogenic factors can be covalently bound to a vascular graft surface in order to prevent acute thrombosis and potentiate cellular ingrowth across the graft. In a preferred embodiment, the biocompatible Dacron™ vascular graft of the invention possesses both surface bound antithrombin and mitogenic properties via covalent linkage of the potent antithrombin agent rHir (to inhibit thrombin activity) and the endothelial cell specific growth factor VEGF (to enhance endothelial cell proliferation) to the polyurethane sealant.

Polyurethanes have unique mechanical and biological properties (i.e., inherent toughness, flexibility, excellent biocompatibility) that make them ideal for use in a wide variety of implantation devices. Polyurethanes are used in many biomedical applications, including ventricular assist devices, access shunts, vascular grafts, and stents. Polyurethanes can be divided into three major groups depending on the choice of macroglycol used to prepare the polymer: polyester-based polyurethanes, polyether-based polyurethanes, and polycarbonate-based polyurethanes. Polycarbonate-based urethanes are stiffer and less compliant than polyether-based polyurethanes with equal hard segment concentration. This is believed to be due to the rotational stiffness imparted by the carbonate linkage (O—C=OO) versus the freedom of the ether linkage (C—O—C). In order to maintain a wide latitude for formulation development (i.e. increase hard segments, more functional groups for attachment) while preserving a narrow range of compliance, it is desirable to utilize more compliant ether macroglycol formulations or ether/carbonate macroglycol (CAS Registry Number 92538-66-4) formulations.

The biostability of polyurethanes has been vigorously studied. See, e.g., Stokes, K., *Advances in Biomedical Polymers*, Proc. Natl. Acad. Sci., Plenum Press, N.Y. (1987). Environmental Stress Cracking (ESC) has been determined to be the main complication associated with implantation of polyurethanes. The two primary factors contributing to ESC of polyurethanes are (1) the presence of an applied strain (must be greater than 100%) and (2) the presence of ether linkages. The elimination of either of these factors will stabilize the polymer against ESC. The first factor can be eliminated by ensuring that minimal strain is present in the final product. This can be accomplished by manufacturing parts using a solution coating process. Annealing, the process of solvent evaporation at elevated temperatures, may also be used since annealed polymers generally do not exhibit ESC in vivo. Zhao, Q. et al., *J. Biomed. Mater. Res.* 29:467 (1995). Thus, solvent processing alone can largely eliminate ESC.

The presence of ether linkages also effects ESC of polyurethanes. Both commercial polycarbonate and polyether urethanes contain ether linkages. In polycarbonate urethanes applicable for vascular uses (Shore hardness range of about 75 to 90 Å) the percent of ether linkages is low (4 to 12%) and thus less susceptible to ESC. Unstabilized polycarbonate urethanes have been shown to be susceptible to ESC in vivo. Therefore, in long-term clinical applications, chemical and/or other methods of stabilization may be needed if the ether linkages cannot be totally eliminated.

ESC initiates as surface phenomena and various approaches have been employed to slow the onset. These include the use of antioxidants, preparation of copolymers such as urethane/silicone polymers in attempts to mask the ether group, and formulating morphological changes to exclude the ether group from the surface. See, e.g., Zhang, Z., et al., *Biomaterials* 16(5):369 (1995), and Ward, R. S., et al., "The effects of phase separation and endgroup, chemistry on in vivo biostability of polyurethane." Trans ASAIO Meeting, Washington, D.C., Lippincott-Raven, Philadelphia, Pa. (1996). Recent efforts using vitamin E as an antioxidant in polyether urethanes have shown that vitamin E prevents ESC in vivo. Collier, T., et al., *J Biomed. Mater. Res.* 41(2):192 (1998). This antioxidant offers many desirable characteristics; it is biocompatible, it has low water solubility (less extractable by the blood), and it has been shown through its many years of use as a commercial polymer stabilizer to be thermally stable. Thus, vitamin E is a good choice as an antioxidant and can be used in the solvent drying processes.

It is believed that ESC is caused by the extraction of a hydrogen that is bonded to the carbon in the alpha position to the oxygen atom. Therefore, synthesizing a polyurethane that excludes this group from the biologic interface through morphological changes is desirable and should give additive if not synergistic (use of vitamin E) protection against ESC. This makes polyether urethane a good choice because of its greater latitude in formulating. In a given compliance (stiffness) range, the hard segment, diisocyanate/short chain extender can be increased 20% more for the polyether urethane than it can for the polycarbonate urethane counterpart. Increasing the hard segment while maintaining the same compliance range provides a two-fold advantage. First, the concentration of the chain extender that contains the functional carboxylic acid groups is increased allowing for greater biological binding. Second, increasing the hard segment necessarily reduces the more susceptible soft segment. More importantly, the surface morphology for a polyurethane having a hard segment greater than 50% is exclusively urethane or urea bonds. These have been proven stable to the biological environment as shown by the absence of ESC in polyether urethane of 55D hardness. Schubert, M. A., et al., *J. Biomed. Mater. Res.* 32:493 (1996).

The polyether or polyether/carbonate based urethane of the present invention contains functional groups, such as carboxylic acid groups, which can be used as anchor sites for protein binding. This ionic polyurethane can be used as a sealant to seal a wide variety of biocompatible devices and implants, including polyethylene terephthalate (polyester or Dacron™) vascular grafts, as well as other types of vascular grafts. It can seal the graft interstices, maintain the physical properties of the Dacron™ scaffolding, and permit covalent linkage of antithrombin (recombinant hirudin or rHir) or other anti-clotting agents, thrombolytic agents (e.g. streptokinase, urokinase, tPA, pro-urokinase, etc.), and mitogenic agents (e.g. vascular endothelial growth factor or VEGF) or other growth promoting substances (e.g. basic or acidic fibroblast growth factor, platelet-derived growth factor, etc.) or inhibitors (e.g. γ-interferon). Surface modification with biologically active proteins can, in part, emulate some of the natural properties of native vessels, thereby improving graft patency and healing. Inhibition of the enzymatic chemotactic and mitogenic properties of thrombin via surface bound anti-clotting factors can significantly reduce blood product formation and maintain anastomotic smooth muscle cells in the quiescent state, thereby preventing the formation of anastomotic intimal hyperplasia. Covalent linkage of growth factors permits complete endothelialization of the graft surface by both trans-anastomotic and trans-membrane (through the remaining residual porosity) cellular migration.

The polyether or polyether/carbonate based urethane polymers of the invention can be obtained by first forming a diisocyanate terminated prepolymer, based on a polyether glycol or a polyether/carbonate glycol having a molecular weight between 200–3,000 Da (preferably between 500–2, 500 Da; most preferably about 1000 Da), and a diisocyanate having the general structure OCN—R'—NCO, wherein R' is a hydrocarbon that may include aromatic or non-aromatic structures, including aliphatic and cycloaliphatic structures. This is followed by chain extension using a dihydroxy carboxylic acid, for example, 2,2-bis(hydroxymethyl)-propionic acid (DHMPA). Polytetramethylene ether glycol (PTMEG 1000) is the preferred polyetherglycol, and the preferred polyether/carbonate macroglycol is polyetherpolycarbonatediol 1000 molecular weight.

The preferred isocyanates include methylene diisocyanate, 4,4'-methylene bisphenyl isocyanate, 4,4'-diphenylmethane diisocyanate (MDI), and hydrogenated methylene diisocyanate (HMDI). Other suitable isocyanates include, but are not limited to, hexamethylene diisocyanate and the toluene diisocyanates, such as 2,4-toluene diisocyanate and 2,6-toluene diisocyanate, 4,4'-tolidine diisocyanate, m-phenylene diisocyanate, 4-chloro-1,3-phenylene diisocyanate, 4,4-tetramethylene diisocyanate, 1,6-hexamethylene diisocyanate, 1,10-decamethylene diisocyanate, 1,4-cyclohexylene diisocyanate, 4,4'-methylene bis (cyclohexylisocyanate), 1,4-isophorone diisocyanate, 3,3'-dimethyl-4,4'-diphenylmethane diisocyanate, 1,5-tetrahydronaphthalene diisocyanate, and mixtures of such diisocyanates. Also included among the isocyanates suitable to this invention are specialty isocyanates containing sulfonated groups for improved hemocompatibility and the like.

A preferred solvent for this process is dimethyl acetamide (DMAC). Other suitable solvents that can be used in this process include, but are not limited to, DMF, THF, cyclohexanone, m-pyrol, etc. Stannous octoate is preferably used as a catalyst. Other catalysts may be used, such as dibutyl tin dilaurate, or generally an organo tin catalyst which is non-toxic and readily hydrolyzes.

The polyether or polyether/carbonate based urethane polymers resulting from the preferred method of synthesis contain carboxylic acid groups within the polymer backbone (PEU-COOH), and have more compliant mechanical properties (i.e. elasticity) than polycarbonate-based urethanes. The synthesis method can be modified to produce a urethane polymer having different functional groups within the polymer backbone. This can be accomplished by, for instance, chain extension with amine groups or photoactive groups.

The invention also features a method of sealing a vascular graft with polyurethane using a modified perfusion system. The vascular grafts of the present invention can be made according to the following steps. First, the graft, preferably a Dacron™ double velour vascular graft, is scoured and washed. The graft is then hydrolyzed, rinsed and dried. Knitted or woven grafts may be used. In a preferred embodiment, the grafts are warp knit (Meadox Medicals, Oakland, N.J.). Examples of other suitable grafts which are commercially available include weft knit, reverse locknit, locknit, or sharkskin grafts.

In one embodiment of the invention, the PEU-COOH is incorporated throughout the wall of the graft using an inward/luminal perfusion system. An example of this perfusion system is shown in FIG. 1. The system includes a flow chamber 1 having an inflow fixture 2 and an outflow fixture 3 in order to circulate polyurethane throughout the system. The flow chamber also includes a porous hollow inner mandrel 4 attached to tubing connectors via microglan clamps.

The system also includes a Y-fitting 5. One part of the Y-fitting 5 is connected to the outflow connector 3 of the flow chamber 1 with hollow plastic tubing, preferably inert Tygon tubing (¼" ID). Another part of the Y-fitting 5 is connected to a peristaltic pump 6, which in turn is connected to the inflow connector 2 of the flow chamber 1. The final part of the Y-fitting is connected to a container 7 holding the PEU-COOH solution. The percent solids in solution may vary from about 1% to about 10%, preferably between 5–7.5%.

The hydrolyzed graft is fitted to the mandrel and tied (e.g. via 2-0 silk), followed by insertion into the flow chamber of the perfusion system. After perfusion, the graft is removed from the flow chamber and air dried, preferably at about 60° C. for approximately 1.5 hours. The graft is then subjected to infusion to uniformly coat the luminal surface. The graft is infused with a solution of PEU-COOH using a programmable infusion system. Again, the percent solids in solution may vary from about 1% to about 10%, preferably between 5–7.5%. After perfusion, the graft is air-dried at about 60° C. for approximately 1.5 hours. This inward/luminal perfusion technique results in a PEU-COOH sealing of the Dacron™ graft (PEU-D). The graft has good flexibility and kink resistance, with PEU-COOH coated evenly on both the lumenal and capsular surfaces of the graft. See FIG. 3.

The surface of the vascular graft of the invention can be modified with biologically active proteins in order to emulate some of the natural properties of native vessels, thereby improving graft patency and healing. For example, the enzymatic, chemotactic, and mitogenic properties of thrombin can be inhibited by surface bound rHir (recombinant hirudin). This inhibition can significantly reduce blood product formation and maintain anastomotic smooth muscle cells in the quiescent state, thereby preventing the formation of anastomotic intimal hyperplasia. rHir has been shown to have potent antithrombin activity when covalently immobilized onto a Dacron™ surface (see, e.g., Phaneuf, M. D., et al., *Biomaterials* 18(10):755 (1997) and Berceli, S. A., et al., *J. Vasc. Surg.* 27:1117 (1998)) or to another biomolecule (see, e.g., Phaneuf, M. D., et al., *Thromb. Haemostas.* 71(4):481 (1994)). In addition, covalent linkage of VEGF (vascular endothelial growth factor) may permit complete endothelialization of the graft surface by both trans-anastomotic and trans-membrane (through the remaining porosity) cellular migration. Techniques for binding growth promoting factors to biocompatible materials are described in U.S. Ser. No. 09/139,507 entitled "Growth-Promoting Biocompatible Substances and Methods of Use Thereof," and in Kubaska, S. M. III, et al., *Surgical Forum* 49:322 (1998), which are herein incorporated by reference.

Covalent linkage of protein to a biomaterial surface in order to create a "basecoat" layer has numerous beneficial advantages. Non-specific or covalent attachment of a protein coating can "passivate" a surface that is relatively thrombogenic, thereby decreasing adhesion of blood products such as platelets, red blood cells, and fibrinogen. Rumisek, J., et al., *Surgery* 105:654 (1989). Proteins incorporated as a basecoat layer can be used as a "scaffolding" in order to promote a specific response such as linkage of RGD peptides to promote cell adhesion. Lin, H. B., et al. *J. Biomed. Mater. Res.* 28:329 (1994). Additionally, increasing the angstrom distance between a biologically-active molecule and the surface via polyethylene oxide groups can reduce steric hindrance on the target molecule, thereby maintaining activity. Park, K. D., et al., *J Biomed. Mater. Res.* 22:977 (1988).

Covalent linkage of a protein "basecoat" layer can serve as the spacer between rHir/VEGF and the biomaterial surface. In one embodiment of the invention, albumin is used as the basecoat moiety. Albumin, which is in natural abundance in circulating blood, has numerous beneficial results in vitro and in vivo. Kotteke-Marchant, K., et al., *Biomaterials* 10:147 (1989) and Phaneuf, M. D., et al., *J Applied Biomater.* 6:289 (1995). Utilization of a basecoat layer permits significant amplification of potential binding sites for secondary protein attachment via heterobifunctional crosslinkers, creating a biomaterial surface with distinct properties for a specific application and has been shown to have numerous binding sites for rHir. Phaneuf, M. D., et al. *ASAIO J.* 44:M653 (1998) and Phaneuf, M. D., et al., *Biomaterials* 18(10):755 (1997). Examples of other basecoat proteins include, but are not limited to, collagen and fibronectin. Alternatively, the basecoat may be synthetic, such as, for example, a Lys-Tyr moiety or polyethylene oxide.

One of the advantages of the present invention is a reduction in the inflammatory response that often results from the implantation of a synthetic device into a patient. In particular, implantation devices made of Dacron™ often elicit an inflammatory response, which may interfere with the overall healing of the graft surface. In contrast, non-extruded polyether-based urethane generally elicits a minimal inflammatory response compared to that of Dacron™ fibers due to antioxidants incorporated into the polymer solution. Thus, when the polyurethane of the invention is used to seal Dacron™ grafts it helps to "mask" the Dacron™ scaffold from immune response.

The Dacron™ vascular grafts of the invention are useful as replacements or bypasses in large and small diameter clinical arterial reconstructions. The invention is also useful as a hemodialysis access graft due to the sealing properties of the polyurethane, or as a sealant for the Dacron™ cuff sewn onto heart valves. Furthermore, the sealing technique of the present invention can be used to seal woven grafts, thereby preventing fraying upon cutting, a major problem when using such structures clinically.

The features and other details of the invention will now be more particularly described and pointed out in the examples. It will be understood that the particular embodiments of the invention are shown by way of illustration and not as limitations of the invention. The principle features of this invention can be employed in various embodiments without departing from the scope of the invention.

EXAMPLE 1

Synthesis of a Polyether and Polyether/Carbonate Urethane Polymers With Carboxylic Acid Groups (PEU-COOH) or (PEC-COOH)

A biodurable polyether-based polyurethane compound containing carboxylic acid groups was synthesized by a two step procedure. The first step involved the formation of diisocyanate terminated prepolymer, based on 1000 Da (molecular weight) polytetramethylene ether glycol (PTMEG 1000) and 4,4'-diphenylmethane diisocyanate (MDI). This was followed by chain extension by 2,2-bis (hydroxymethyl)-propionic acid (DHMPA). Dimethyl acetamide (DMAC) was used as the solvent and stannous octoate as a catalyst.

A 1000 nominal molecular weight polyether polyol (117.0 g containing 0.117 moles–hydroxyl content=112.2 mg KOH) and 62.5 g (0.25 moles) of MDI was charged to a reaction kettle and stirred for 1.5 hours at 75° C. under a dry, inert $N_2$ atmosphere. DMAC (502.9 g) was then added and reaction temperature lowered to 65° C. with constant stirring for an additional 1 hour. DHMPA (18.8 g, 0.14 moles) and five drops of stannous octoate were added to the reaction mixture and the temperature adjusted to 60° C. This temperature was held for an additional 2 hours, then the reaction mixture was slowly cooled to ambient temperature while mixing continued. The resulting solution, approximately 28% weight, was transferred into a wide-mouth jar and stored under a dry nitrogen blanket. This polymer was designed to contain approximately 3.2% (weight) of reactive carboxyl groups. Films (0.1 mm) were then cast from the 15% solids solution onto release paper to grossly evaluate the presence of carboxylic acid groups via methylene blue uptake, and to macroscopically assess physical parameters.

In a similar fashion, a Biodurable poly(ether/carbonate)-based polyurethane containing carboxylic acid groups was synthesized by the two step procedure utilizing: 1) formation of diisocyante terminated prepolymer, based on 1000 Da (molecular weight) polyetherpolycarbonatediol (CAS Registry Number 92538-66-4) and 4,4'-diphenylmethane diisocyante (MDI) followed by 2) chain extension by 2,2-bis (hydroxymethyl)-propionic acid (DHMPA). Dimethylacetamide (DMAC) was used as the solvent and stannous octoate as catalyst.

A 1010 nominal molecular weight polyetherpolycarbonatepolyol (118.3 g) containing 0.117 moles (hydroxyl content=111.0 mg KOH) and 64.25 g (0.257 moles) of MDI was charged to a reaction kettle stirred for 1.5 hours at 75° C. under a dry, inert $N_2$ atmosphere. DMAC (517.8 g) was then added and reaction temperature lowered to 65° C. with constant stirring for an additional 1 hour. DHMPA (18.8 g, 0.14 moles) and five drops of stannous octoate were added to the reaction mixture and the temperature adjusted to 60° C. This temperature was held for an additional 2 hours, then the reaction mixture was slowly cooled to ambient temperature while mixing continued. The resulting solution, approximately 28% weight, was transferred into a wide-mouth jar and stored under a dry nitrogen blanket. This polymer was designed to contain approximately 3.2% (weight) of reactive carboxyl groups. Films (0.1 mm) were then cast from the 15% solids solution onto release paper to grossly evaluate the presence of carboxylic acid groups via methylene blue uptake, as described under the preceding chemical characterization section, and to macroscopically assess physical parameters.

The processes resulted in either a polyether (PEU-COOH) or a polyetherpolycarbonate (PEU-COOH)-based urethane polymer with carboxylic acid groups. Both of which possess more compliant mechanical properties (i.e., elasticity) than previously utilized polycarbonate-based urethanes. Carboxylic acid groups were also determined to be accessible within the polymer structures via methylene blue uptake (data not shown).

EXAMPLE 2

Sealing of a Knitted Dacron™ Double Velour Vascular Graft With PEU-COOH

Graft Preparation

Knitted Dacron™ double velour vascular grafts (100 cm length) were scoured in a 1 L Tween 20/sodium carbonate solution at 60° C. for 30 minutes followed by a distilled water wash at 60° C. for 30 minutes. Grafts were then hydrolyzed by exposing the graft to 1% sodium hydroxide at 100° C. for 30 minutes. The grafts were rinsed with distilled water and dried at 80° C. for 1 hour. After drying, the grafts were cut into segments (15 cm) that were used for each perfusion.

Inward/Luminal Perfusion System

A perfusion system shown in FIG. 1 was used in order to incorporate PEU-COOH (as prepared in Example 1) throughout the wall of the graft. This system included a 60 ml polyethylene chamber with inflow and outflow fixtures in order to circulate polyurethane throughout the system. Connected to the chamber was a porous, hollow inner polyethylene mandrel attached to 6 mm tubing connectors. The hydrolyzed graft segment was connected to this fitting via 2-0 silk and inserted into the flow chamber through a pre-fit seal secured with Teflon tape. A cover was placed over the top of the chamber in order to stabilize the upper connector. Inert Tygon tubing (¼" ID) was fitted over the upper (withdrawal) connector, followed by attachment to a Y-fitting. One part of the Y-fitting was connected to a Harvard Apparatus peristaltic pump that continued onto the side connector (inlet feed) of the chamber, thereby completing the perfusion loop. Tygon tubing was connected to the other part of the Y-fitting which was inserted into a 7.5% solids PEU-COOH solution. The flow rate was 12 ml/min and the system was run for 1 hour. After perfusion, the graft was removed from the chamber with one connector remaining attached and air-dried at 60° C. for 1.5 hours.

The connector/graft segment was then attached to a 60 ml syringe that had an 8 mm connector on the outflow end. The syringe was filled with a 7.5% solids solution of PEU-COOH and placed into a Harvard Apparatus PHD 2000 Programmable Infusion System. The graft was set in a downward position prior to infusion and clamped at the end of the graft in order to uniformly coat the luminal surface.

A flow rate of 20 ml/min was employed. Once the graft was filled, the clamp was immediately released. Flow was then permitted to continue unhindered for the remainder of the run. The graft was removed from the system and air-dried at 60° C. for 1.5 hours.

Macroscopically, PEU-COOH sealing of Dacron™ grafts using this inward/luminal perfusion technique resulted in a flexible vascular graft with good kink resistance. Additionally, the PEU-COOH coating was evenly distributed on both surfaces, a significant improvement over previous sealing techniques. There were also no apparent air bubbles trapped within the graft wall.

EXAMPLE 3

Physical and Chemical Characterization of PEU-D Grafts

Physical Characterization

Water permeation for cleaned (CNTRL), HEMASHIELD™, and PEU-D grafts (7.5%/7.5%, 5.0%/7.5% and 5.0%/5.0%) (as prepared in Example 2) was determined using a previously described procedure. Sawyer, P. N., et al., *J. Biomed. Mater. Res.* 13:937 (1979). Grafts (6 mm, ID) of each material were opened and cut into circular segments (15 cm diameter). A cylindrical reservoir, with a direct water inlet to keep pressure constant, was set to a height of 165 mm to the top of the water column. Polypropylene tubing (¼" ID) was run from the bottom of the reservoir and connected to a T-shaped fitting. One part of the fitting was connected to tubing that was attached to a manometer, permitting accurate determination of pressure directly at the sample/water interface. The other part was attached to the sample chamber. A $5/16$" Tight Right fitting (attached to $3/16$" tubing) was used to hold the test segment in place without applying stretch to the material. The area of material exposed to flow was calculated to be 0.38 $CM^2$ and was constant for all samples. A hemostat was used to maintain stasis between sample changes. Each segment of material was pre-soaked in the apparatus for 1 minute in order to de-gas. All graft segments were exposed to 120 mm Hg pressure. The CNTRL segments, due to the high water permeability, had to begin at 180 mm Hg at stasis in order to maintain pressure constant upon water release. The Hemashield graft segments (cross-linked collagen impregnated) and PEU-D segments were exposed to 120 mm Hg pressure without alteration. CNTRL segments were evaluated for 30 seconds and Hemashield/PEU-D for 60 seconds. Volume was collected in a graduated cylinder and was used to determine ml/min/$cm^2$.

Figure 2:
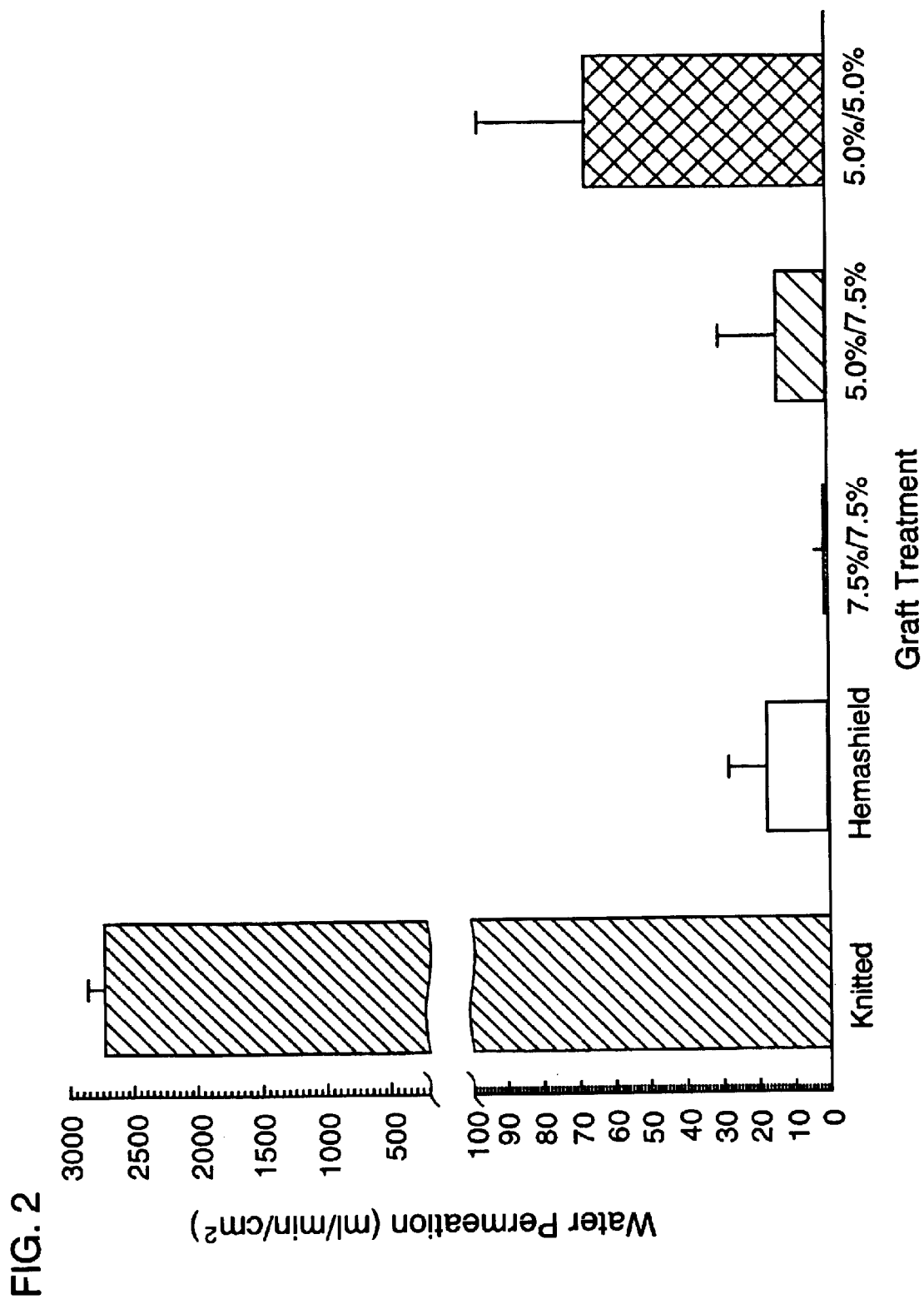
FIG. 2 is a bar graph showing water permeation data for selected vascular grafts.

Water permeation by PEU-D grafts sealed with either 7.5%/7.5% (0.44±0.38 ml/min/$cm^2$) or 5.0%/7.5% (13±17 ml/min/CM2) solids had comparable water permeation to collagen cross-linked Hemashield grafts (17±11 ml/min/$cm^2$), as shown in FIG. 2. Water permeation using the 5.0%/5.0% parameters (67±30 ml/min/$cm^2$) was higher than the Hemashield grafts, however, implantation of grafts with permeation values of less than 100 ml/min/$cm^2$ has been performed without bleeding complications. The mean permeation reported for Hemashield grafts was <10 ml/min/$cm^2$, thereby demonstrating the accuracy of the test method. CNTRL segments were essentially ineffective at blocking water permeation (2,717±140 ml/min/$cm^2$), with this value slightly higher than the reported mean permeability of 1,900 ml/min/$cm^2$.

Chemical Characterization

Methylene blue (MB), a cationic dye that has been employed to determine carboxylic acid groups within both Dacron™ and polyurethane (see, e.g., Dempsey, D. J., et al., *ASAIO J* 44:M506 (1998)), was used to quantitatively and qualitatively assess carboxylic acid content in the PEU-D grafts. A 500 ml stock solution (500 µg/ml) of methylene blue was prepared (80% Purity) in 0.1 M Tris-CL pH 8.0. A working solution of methylene blue was prepared by aliquotting 1 ml of the stock solution and bringing to a total volume of 100 ml with Tris buffer (5 µg/ffil). Segments (0.5 cm) were cut from knitted, 0.5% sodium hydroxide-hydrolyzed (HYD), and 3 PEU-D sealed grafts (n=4/test group). Working MB solution (10 ml) was added to each segment, and incubated for 1 hour. Grafts were removed and placed into wash solution consisting of Tris buffer for one hour. Dye bath and wash solutions were read at 611 nm using Tris buffer as blank. Quantification of carboxylic acid groups within each graft (nmoles/mg) was calculated using standard equations as previously described.

Figure 3:
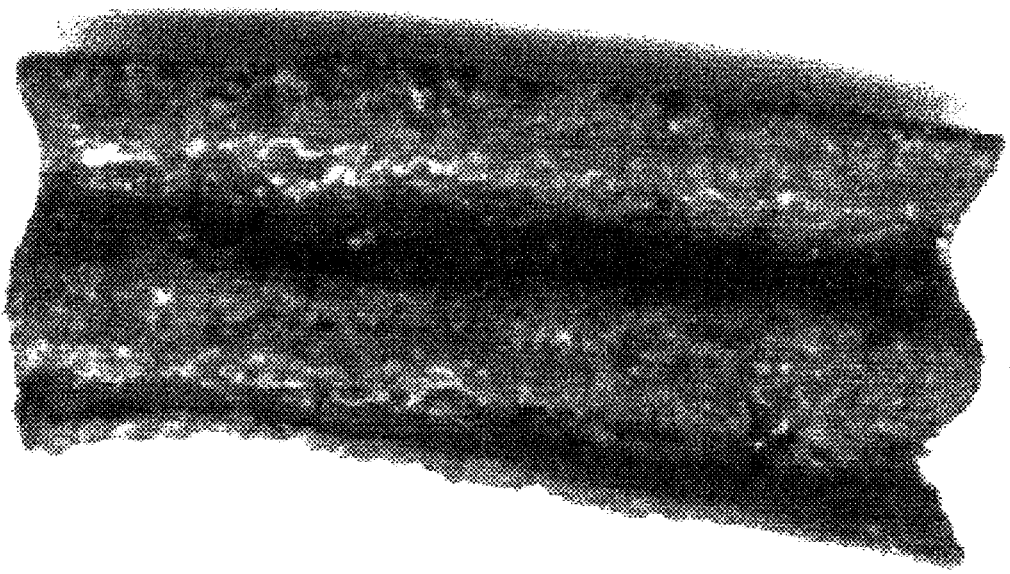
FIG. 3 is a picture of the lumenal surface and capsular surface of a Dacron™ graft sealed with a PEU-COOH coating.
Figure 3:

The amount of carboxylic acid groups created on the PEU-D segments (1.04±0.27, 0.92±0.07, and 0.86±0.06 nmoles/mg, respectively) was significantly greater than both HYD (0.43±0.7 nmoles/m g) and CNTRL (0.24±0.05 nmoles/mg) segments, respectively. Microscopic evaluation of methylene Blue-dyed PEU-D grafts revealed a uniform seal that extended throughout the graft wall. Additionally, both surfaces showed comparable PEU-COOH coating, as seen in FIG. 3.

EXAMPLE 4

Covalent Linkage of a Basecoat Protein Canine Serum Albumin to the PEU-D Graft Surface $^{125}$I-canine serum albumin (CSA) binding versus CNTRL, HYD, and PEU-D segments (3 treatments) was performed to determine basecoat binding. Phaneuf, M. D., et al., *Biomaterials* 18(10):755 (1997) and Phaneuf, M. D., et al., *J Biomed. Appl* 12:100 (1997). Graft segments (0.5 cm) were cut and weighed (n=4/test group/condition). One set of each graft type was placed into 5 ml of a 10 mg/ml (50% ethanol) solution of EDC crosslinker. The control segments of each group were placed into 5 ml of 50% ethanol solution. A total of 4 segments/tube were used for all protein binding assays. All segments were reacted for 30 minutes at room temperature on an inversion mixer. Segments were then removed from their respective solutions, shaken to remove excess solvent/crosslinker and placed into 2.4 ml of a 14.8 µM $^{125}$I-CSA, radiolabeled. These segments were incubated for 2 hours at room temperature on an inversion mixer. Control and test segments of each were removed and placed into individual test tubes containing 2 ml of PBS with 9% Tween 20. These polyurethane segments were sonicated in an ultrasonic cleaner for 5 minutes. This procedure was repeated 3 times followed by 2 additional washes for 15 minutes, with the wash buffer changed between sonications, in order to remove any weakly adherent $^{125}$I-CSA on the segment surface. Segments with non-specifically bound (CNTRL+$^{125}$I-CSA, HYD+$^{125}$I-CSA, and PEU-D+$^{125}$I-CSA) and covalently bound (CNTRL−$^{125}$I-CSA, HYD−$^{125}$I-CSA, and PEU-D−$^{125}$I-CSA) $^{125}$I-CSA were then gamma counted. Utilizing the specific activity, the amount of $^{125}$I-CSA bound (ng) per weight of graft segment (mg) was determined. Results are shown in FIG. 4.

Figure 4:
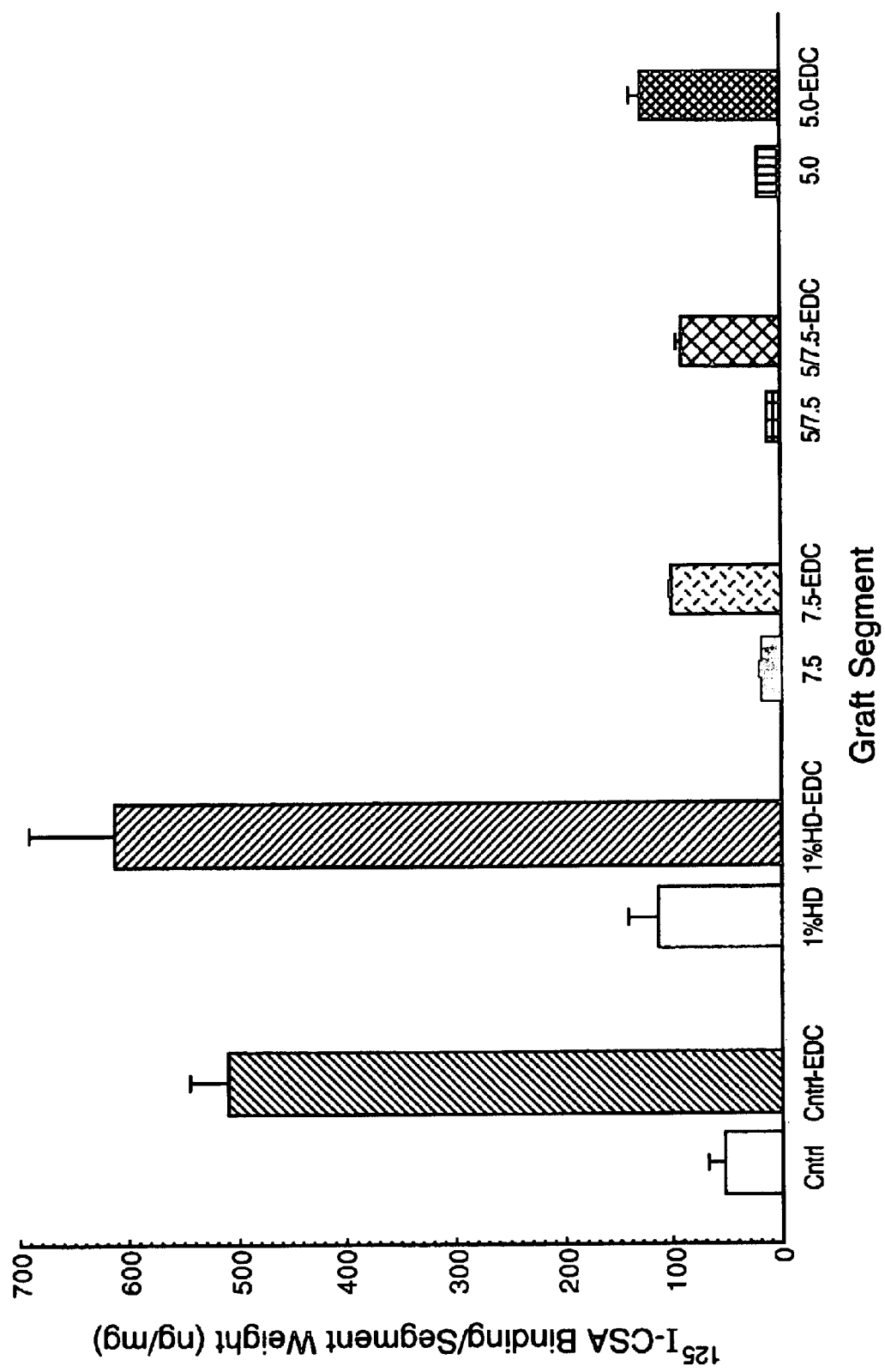
FIG. 4 is a bar graph showing $^{125}$I-CSA binding data for selected vascular grafts.
Figure 4:
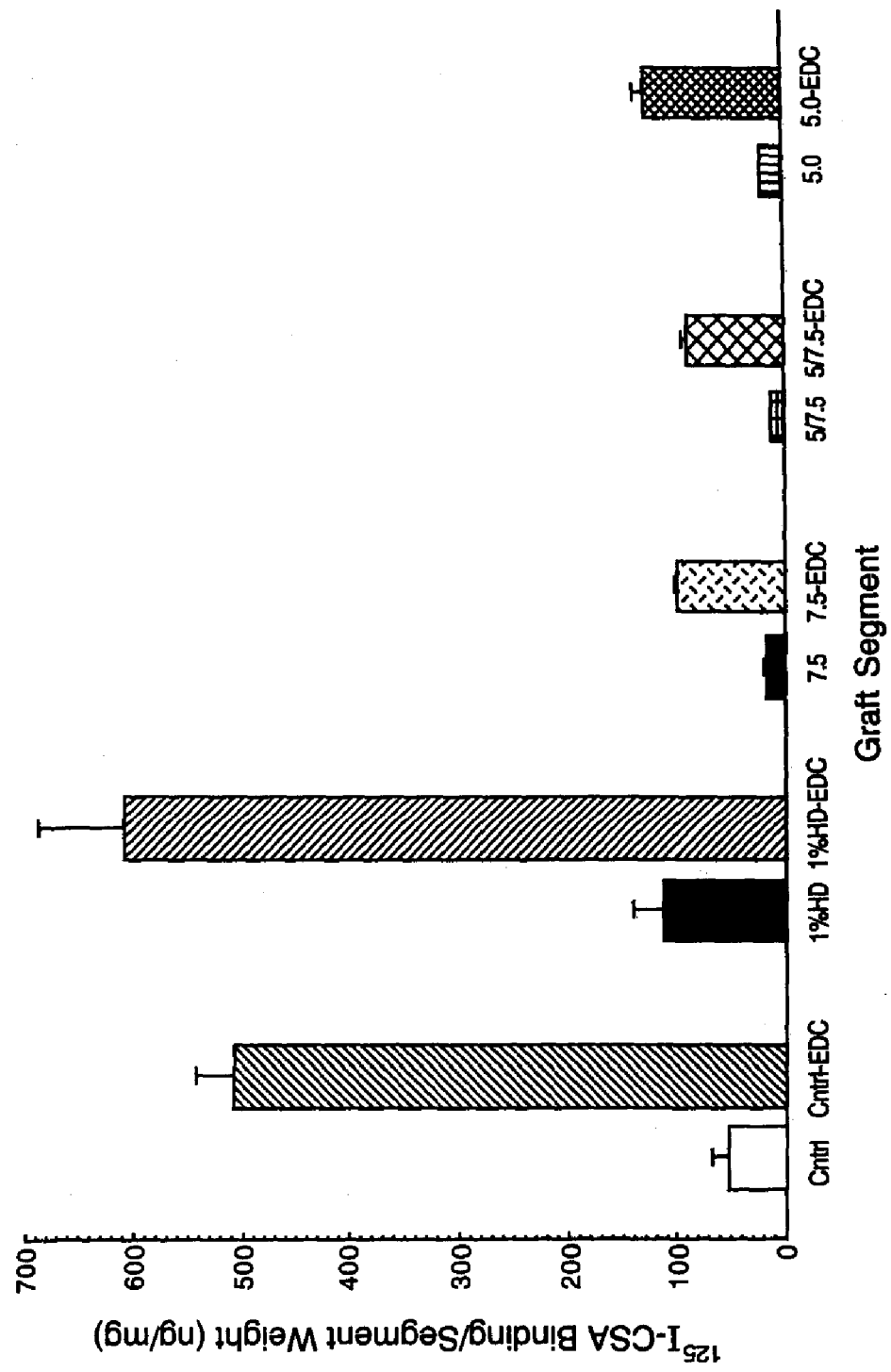

Non-specific binding of $^{125}$I-CSA to HYD segments (115±27 ng/mg) was greater than CNTRL (54±13 ng/mg) and PEU-D (18±3, 13±0.8, and 20±2 ng/mg, respectively) segments, with the PEU-D segments binding the lowest amount of $^{125}$I-CSA (FIG. 4). Therefore, PEU coating significantly reduced non-specific protein adhesion. Covalent linkage of $^{125}$I-CSA was also greatest in the HYD segments (613±77 ng/mg) as compared to CNTRL (509±36 ng/mg) and PEU-D (103±2, 90±7, and 129±11 ng/mg, respectively) segments. The lower amount of $^{125}$I-CSA bound is believed to be attributed to a reduced total surface area by the polyurethane sealant. Reduction in CSA adhesion could result in lowering non-specific binding of other blood products such as fibrinogen, platelets or thrombin that are detrimental to graft patency.

EXAMPLE 5

In vivo Assessment of PEU-COOH Sealed Dacron™ Grafts

Mongrel canines (25–30 kg) were sedated with acepromazine (0.75 mg/kg), induced with pentothal and maintained on halothane gas (0.5–1.5%). Through a midline incision, the carotid arteries were exposed for a length of approximately 15 cm. Following heparinization (100 units/kg), a 6 mm, 5.0%/7.5% PEU-COOH sealed Dacron™ graft (6 cm length, gamma sterilized) was implanted on one side and a 6 mm 5.0%/5.0% PEU-COOH sealed Dacron™ graft (6 cm length, gamma sterilized) was implanted on the contralateral side. The grafts were re-exposed at 1 week and punctured with a 16-gauge needle to determine the self-sealing properties of the graft. The grafts were then excised and evaluated for patency, gross thrombus and pseudointima formation.

The graft handling properties were comparable in both stiffness and suturing, with a favorable rating from both surgeons. Grafts did soften upon soaking in saline prior to suturing. Needle puncturing of both grafts showed self-sealing of the puncture site within seconds of needle removal. Both grafts were patent at 1 week. Upon macroscopic evaluation, the surface had uniform pseudointima formation, with composition to be determined via histological analysis.

Equivalents

Although the present invention has-been described with reference to preferred embodiments, one skilled in the art can easily ascertain its essential characteristics and without departing from the spirit and scope thereof, can make various changes and modifications of the invention to adapt it to various usages and conditions. Those skilled in the art will recognize or be able to ascertain using no more than routine experimentation, many equivalents to the specific embodiments of the invention described herein. Such equivalents are intended to be encompassed in the scope of the present invention.

All publications, patents, and patent applications, mentioned in this specification are herein incorporated by reference.

What is claimed is:

1. A biocompatible device adapted for therapeutic use within the body of a mammal, said device comprising:
   (a) a polymeric base; and
   (b) a surface layer coating said polymeric base, said surface layer coating comprising a polyether or polyether/carbonate based urethane polymer having carboxylic acid groups serving as anchor sites prepared by a method comprising the steps of:
      (i) forming a diisocyanate terminated prepolymer based on (i) a polyether glycol or polyether/carbonate glycol having a molecular weight between about 200 to 3,000 Da and (ii) a diisocyanate having the general structure OCN—R'—NCO, wherein R' is a hydrocarbon; and
      (ii) chain extending said prepolymer using a dihydroxy carboxylic acid.

2. The device of claim 1, wherein said device is a vascular graft and said polymeric base is a graft wall base, wherein said surface layer coating coats the inner or outer surface of said graft wall base.

3. The device of claim 2, wherein said graft wall base comprises polyethylene terephthalate, polyurethane, polyethylene, polypropylene, silicons, or nylon.

4. The device of claim 3, wherein said graft wall base is a knitted polyethylene terephthalate double velour vascular graft.

5. The device of claim 2, wherein said surface layer coating additionally comprises a covalently-attached protein.

6. The device of claim 5, wherein said protein is selected from the group consisting of an anti-clotting agent, a thrombolytic agent, a mitogenic agent, a growth promoting substance, and an inhibitor.

7. The device of claim 6, wherein said mitogenic agent is vascular endothelial growth factor (VEGF) and said anti-clotting agent is recombinant hirudin (rHir).

8. The device of claim 2, wherein said graft has a vascular shape with an internal diameter between about 2.0 and 20.0 mm.

9. The device of claim 8, wherein said graft has a vascular shape with an internal diameter between 6.0 and 8.0 mm.

10. The device of claim 2, wherein said graft has a vascular shape with an internal diameter less than about 9.0 mm.

11. The device of claim 10, wherein said graft has a vascular shape with an internal diameter less than about 6.0 mm.

12. The device of claim 11, wherein said graft has a vascular shape with an internal diameter less than about 5.0 mm.

13. The device of claim 1, wherein said diisocyanate is selected from the group consisting of 4,4'-diphenylmethane diisocyanate (MDI), hydrogenated methylene diisocyanate (HMDI), hexamethylene diisocyanate, toluene diisocyanates, 4,4'-tolidine diisocyanate, m-phenylene diisocyanate, 4-chloro-1,3-phenylene diisocyanate, 4,4-tetramethylene diisocyante, 1,6-hexamethylene diisocyanate, 1,10-decamethylene diisocyanate, 1,4-cyclohexylene diisocyanate, 4,4'-methylene bis (cyclo hexylisocyanate), 1,4-isophorone diisocyanate, 3,3'-dimethyl-4,4'-diphenylmethane diisocyanate, and 1,5-tetrahydronaphthalene diisocyanate.

14. The device of claim 13, wherein said diisocyanate is 4,4'-diphenylmethane diisocyanate (MDI).

15. The device of claim 1, wherein said polyether glycol is polytetramethylene ether glycol (PTMEG 1000).

16. The device of claim 1, wherein said polyether/carbonate glycol is polyetherpolycarbonatediol.

17. The device of claim 1, wherein said carboxylic acid is 2,2-bis(hydroxymethyl)-propionic acid (DHMPA).

18. The device of claim 1, wherein said molecular weight is about 1,000 Da.

19. The biocompatible device of claim 1, wherein said mammal is a human.

\* \* \* \* \*

UNITED STATES PATENT AND TRADEMARK OFFICE
CERTIFICATE OF CORRECTION

PATENT NO. : 6,743,253 B2
DATED : June 1, 2004
INVENTOR(S) : Matthew D. Phaneuf et al.

It is certified that error appears in the above-identified patent and that said Letters Patent is hereby corrected as shown below:

Title page,
Item [56], References Cited, OTHER PUBLICATIONS,
"Fyfe, B. et al." reference, replace "Explained" with -- Explanted --; and
"Hanson, S.R." reference, replace "in" with -- In --.

Drawings,
Sheet 4 of 4, Fig. 4, shade the bar labeled 1%HD and the bar labeled 7.5.

Column 12,
Line 20, replace "m g" with -- mg --.

Signed and Sealed this

Eighth Day of March, 2005

JON W. DUDAS
*Director of the United States Patent and Trademark Office*